United States Patent [19]

Müller et al.

[11] Patent Number: 5,277,739
[45] Date of Patent: Jan. 11, 1994

[54] PROCESS FOR BONDING A MATERIAL TO A COLLAGEN-CONTAINING MATERIAL

[75] Inventors: Michael Müller, Bergisch Gladbach; Wolfgang Podszun, Cologne; Bernd Alker, Bergisch Gladbach, all of Fed. Rep. of Germany

[73] Assignee: Bayer Aktiengesellschaft, Leverkusen, Fed. Rep. of Germany

[21] Appl. No.: 994,043

[22] Filed: Dec. 15, 1992

Related U.S. Application Data

[63] Continuation of Ser. No. 723,730, Jun. 20, 1991, abandoned, which is a continuation of Ser. No. 478,805, Feb. 12, 1990, abandoned, which is a continuation of Ser. No. 389,716, Aug. 4, 1989, abandoned.

[30] Foreign Application Priority Data

Aug. 19, 1988 [DE] Fed. Rep. of Germany ....... 3828169

[51] Int. Cl.$^5$ .............................................. C09J 4/02
[52] U.S. Cl. ................... 156/330.9; 156/331.1; 156/331.3; 156/331.6; 156/331.8; 156/331.9; 433/9; 433/180; 433/226; 523/118; 526/183; 526/208; 526/301; 526/312
[58] Field of Search ............ 156/330.9, 331.1, 331.3, 156/331.6, 331.8, 331.9; 433/9, 180, 226; 523/118; 526/183, 208, 301, 312

[56] References Cited

U.S. PATENT DOCUMENTS

| | | | |
|---|---|---|---|
| 2,793,211 | 5/1957 | LoCicero et al. | 546/245 |
| 4,039,513 | 8/1977 | Naarmann et al. | 528/246 |
| 4,323,696 | 4/1982 | Schmitz-Josten et al. | 560/220 |
| 4,404,327 | 9/1983 | Crugnola et al. | 525/228 |
| 4,479,782 | 10/1984 | Orlowski et al. | 433/9 |
| 4,593,054 | 6/1986 | Asmussen et al. | 523/118 |
| 4,952,241 | 8/1990 | Reiners et al. | 106/35 |
| 4,952,614 | 8/1990 | Reiners et al. | 523/115 |

FOREIGN PATENT DOCUMENTS

| | | |
|---|---|---|
| 0023686 | 2/1981 | European Pat. Off. |
| 3703080 | 1/1988 | Fed. Rep. of Germany |
| 3703130 | 1/1988 | Fed. Rep. of Germany |
| 1410558 | 9/1964 | France |

OTHER PUBLICATIONS

J. Dent. Res. 57, 500–505 (1978).
Scand. J. Dent. Res. 92, 480–483 (1984).
Scand. J. Dent. Res. 88, 348–351 (1980).
J. Dent. Res. 63, 1087–1089 (1984).
Houben-Weyl, Methoden der organischen Chemie, vol. E 20, pp. 80ff, Georg Thieme Verlang Stuttgart 1987.
R. S. Baratz, J. Biomat. Applications, vol. 1, 1987, pp. 316ff.
K. Eichner, "Zahnärztliche Werkstoffe undf ihre Verarbeitung", vol. 2, pp. 135ff, Hüthig Verlag, 5th Edition, 1985.
Dentin Bonding in Perspective, James C. Setcos, American Journal of Dentistry, vol. 1, pp. 173-175 (1988).
Mohr et al., "Technology and Engineering of Reinforced Plastics and Composites", Van Nostrand Reinhold Co., 1973, pp. 149-151.
Rodriguez, "Principles of Polymer Systems", McGraw-Hill Book Co., New York, 1982, pp. 262-263.
Billmeyer, Jr., "Textbook of Polymer Science", Wiley-Interscience, New York, 1984, pp. 138-141, 470-472.

*Primary Examiner*—Joseph L. Schofer
*Assistant Examiner*—R. H. Delmendo
*Attorney, Agent, or Firm*—Sprung, Horn, Kramer & Woods

[57] ABSTRACT

Adhesive component formulations containing (meth)acrylic acid esters, containing formamide groups, and optionally an initiator, which are used as an adhesive component for the treatment of collagen-containing materials.

11 Claims, No Drawings

PROCESS FOR BONDING A MATERIAL TO A COLLAGEN-CONTAINING MATERIAL

This application is a continuation of application Ser. No. 723,730, filed Jun. 20, 1991, now abandoned, which is a continuation of application Ser. No. 478,805, filed Feb. 12, 1990, now abandoned, which is a continuation of application Ser. No. 389,716, filed Aug. 4, 1989, now abandoned.

The invention relates to formulations for use as an adhesive component for the treatment of collagen-containing materials, to a process for preparing them, and to their use.

Collagen-containing materials are scleroprotein substances and main constituents of the human and animal intercellular supporting substances such as cartilage tissue and bone tissue, skin and ebur dentis (dentin). Within the scope of the present invention, the adhesive components are preferably used for the treatment of dentin in connection with tooth repairs.

Especially in the dental field, curing polymeric materials are used as filling materials in tooth repairs. Acrylate-based fillings are in general preferred as the curing polymeric materials. These polymeric fillings, however, have the disadvantage of poor adhesion to the dentin. For solving this problem, undercuts on the dentin have hitherto been made in some cases; for this purpose, it was necessary to remove considerable quantities of fresh dentis, beyond the attacked area.

According to another method, the dentin and the surface of the enamel are incipiently etched with acids such as, for example, phosphoric acid, and the filling is then carried out. Apart from the fact that the acid exerts an irritant action on the buccal region, it also easily penetrates through the dentin canals into the tooth and damages the nerve (pulpa).

In J. Dent. Res. 57, 500–505 (1978), aldehyde group-containing methacrylates of the isomeric hydroxybenzaldehydes are described, which can be used as priming agents for fillings in the dental field. However, the bond between dentin and filling composition remains unsatisfactory even after such priming.

In Scand. J. Dent. Res. 92, 980-983 (1984), and J. Dent. Res. 63, 1087-1089 (1984), priming agents of aqueous formaldehyde or glutaraldehyde and β-hydroxyethylmethacrylate (HEMA) are described.

Moreover, in EP-A-141,324 (U.S. Pat. No. 4,593,054), compositions of an aldehyde and an olefinically unsaturated monomer with active hydrogen are described, which exhibit good bonding to dentin.

Formulations have been found which contain (meth)acrylic acid esters, containing formamide groups, of the formula $$H_2C=C(R^1)-C(=O)-O-X-N(R^2)-C(H)=O \quad (I)$$

in which
$R^1$ denotes hydrogen or methyl,
$R^2$ denotes hydrogen, optionally hydroxy-, carboxy-, halogen- or amino-substituted (amino of the formula $$-N\begin{matrix}R^3\\R^4\end{matrix}$$

in which
$R^3$ and $R^4$ are identical or different and denote hydrogen or lower alkyl) alkyl ($C_1$ to $C_{12}$), aryl ($C_6$ to $C_{12}$) or aralkyl ($C_7$ to $C_{14}$) and
X denotes a divalent, optionally hydroxy-, carboxy-, halogen- or amino-substituted (amino of the formula $$-N\begin{matrix}R^3\\R^4\end{matrix}$$

in which
$R^3$ and $R^4$ have the meaning given above) aliphatic ($C_1$ to $C_{24}$) and/or cycloaliphatic ($C_5$ to $C_8$) and/or aromatic ($C_6$ to $C_{12}$) radical which can optionally contain one or more oxygen bridges, sulphur bridges and/or $-NR^3$-bridges,
$R^3$ having the meaning given above,
and optionally initiators, as an adhesive component for the treatment of collagen-containing materials.

The novel formulations effect a strong bonding adhesion of materials which are to be fixed to the collagen, for example bonding adhesion of tooth-filling material in a cavity in the tooth.

(Meth)acrylic acid esters containing formamide groups are known from DE-A-2,507,189. In DE-A-2,507,189, the use of these acrylic acid esters as coatings or adhesive agents for paper and textiles is also described. The use of the (meth)acrylic acid esters, containing formamide groups, according to the invention as an adhesive component for collagen-containing materials was surprising because they do not contain any reactive groups which would be able to build up suitable chemical bonds to collagen-containing materials under mild conditions.

(Meth)acrylic acid esters within the scope of the present invention are the esters of acrylic acid and methacrylic acid.

The substituents of the (meth)acrylic acid esters according to the invention within the scope of the general formula (I) have in general the following meaning:

Halogen denotes in general fluorine, chlorine, bromine and iodine, preferably fluorine and chlorine.

Lower alkyl ($R^3$ and $R^4$) within the scope of the amino groups denotes in general a straight-chain or branched hydrocarbon radical having 1 to approximately 6 carbon atoms. Methyl and ethyl are preferred.

As the amino groups, amino, dimethylamino, diethylamino and methyl-ethylamino may be mentioned by way of example.

Alkyl ($R^2$) denotes in general a straight-chain or branched hydrocarbon radical having 1 to 12 carbon atoms, preferably 1 to 6 carbon atoms. The following alkyl radicals may be mentioned by way of example: methyl, ethyl, propyl, isopropyl, butyl, isobutyl, pentyl, isopentyl, hexyl and isohexyl. Methyl and ethyl are particularly preferred.

Aryl denotes in general an aromatic hydrocarbon radical which optionally can also be substituted (for example by lower alkyl), having 6 to 12 carbon atoms.

The following aryl radicals may be mentioned by way of example: phenyl, diphenyl, naphthyl and tolyl. Phenyl and tolyl are preferred.

Aralkyl denotes in general an aryl radical having 7 to 14 carbon atoms, which is bonded via an alkylene chain and which can also optionally be substituted (for example by lower alkyl). Aralkyl radicals having 1 to 6 carbon atoms in the aliphatic moiety and having 6 to 12 carbon atoms in the aromatic moiety are preferred. The following aralkyl radicals may be mentioned by way of example: benzyl, naphthyl/methyl, phenethyl, phenylpropyl and methyl-substituted benzyl. Benzyl and methyl-substituted benzyl are preferred.

A divalent aliphatic radical (X) denotes in general a divalent, straight-chain or branched hydrocarbon radical having 1 to 24, preferably 1 to 20 and especially preferably 1 to 10 carbon atoms. The following divalent aliphatic radicals may be mentioned by way of example: dodecanediyl, undecanediyl, decanediyl, nonanediyl, octanediyl, heptanediyl, hexanediyl, 2,3-dimethylbutanediyl, pentanediyl, neopentanediyl, butanediyl, dimethylethanediyl, propanediyl and ethanediyl.

Ethanediyl and propanediyl are preferred as the divalent aliphatic radicals.

A divalent cycloaliphatic radical (X) denotes in general a cyclic hydrocarbon radical having 5 to 8 and preferably 5 or 6 carbon atoms. The following divalent cycloaliphatic radicals may be mentioned by way of example: cyclopentyl, cyclohexyl, cycloheptyl and cyclooctyl. Cyclopentyl and cyclohexyl are preferred. A divalent aromatic radical (X) denotes in general a divalent aromatic hydrocarbon radical having 6 to 12 carbon atoms. The following divalent aromatic radicals may be mentioned by way of example: phenylene, biphenyldiyl and naphthylenediyl. Phenylene is preferred.

The divalent aliphatic, cycloaliphatic and aromatic radicals can be substituted by hydroxy, carboxy, halogen or amino groups. Hydroxy, carboxy, fluorine, chlorine and amino are preferred as substituents. X can in general be substituted by 1 to 10 radicals.

It is also possible, however, that X consists of aliphatic and cycloaliphatic, aliphatic and aromatic, cycloaliphatic and aromatic, or aliphatic, cycloaliphatic and aromatic radicals. In this case the total number of carbon atoms is in the range from 6 to 30, preferably from 6 to 15. Divalent radicals, in which phenylene radicals are linked via methylene bridges, are preferred.

It is also possible, however, that the aliphatic, cycloaliphatic and aromatic radicals in X are linked by oxygen bridges, sulphur bridges and/or —NR$^{13}$ bridges (R$^3$ having the meaning given above). In this case, it is possible that the aliphatic, cycloaliphatic and aromatic radicals are linked in each case only by oxygen or sulphur or —NR$^3$. It is also possible, however, that different bridge members link the aliphatic, cycloaliphatic and aromatic radicals to one another. In this case, the total number of carbon atoms is in the range from 4 to 45, preferably from 4 to 12, and the number of bridge members is in the range from 1 to 20, preferably from 1 to 6. Divalent radicals in which ethylene radicals are linked via oxygen bridges are preferred.

By way of example, the following (meth)acrylic acid esters containing formamide groups may be mentioned:

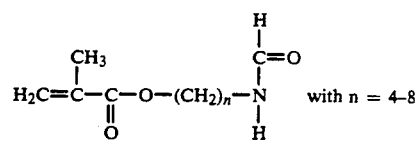

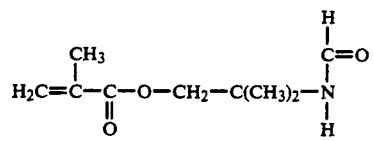

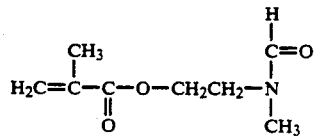

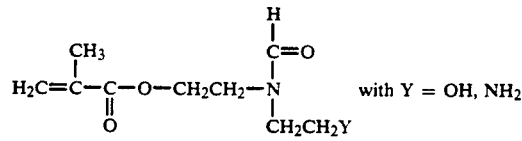

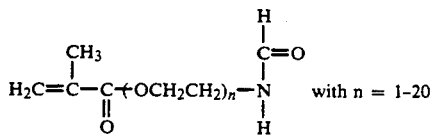

Methacrylic acid 3-formamidopropyl ester and methacrylic acid 2-formamidoethyl ester of the formula

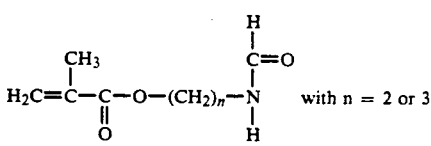

are particularly preferred.

The preparation of the (meth)acrylic acid esters containing formamide groups, according to the invention, is known per se (DE-A-1,770,964 and DE-A-2,507,189). For example, the (meth)acrylic acid esters containing formamide groups can be prepared by reacting alkanolamines with formic acid esters and (meth)acrylic acid chloride.

Initiators within the scope of the present invention are free radical formers which trigger a free-radical polymerization. Photoinitiators, which trigger a free-radical polymerization under the action of light, for example UV light, visible light or laser light, are preferred.

The so-called photopolymerization initiators are known per se (Houben-Weyl, Methoden der organischen Chemie [Methods of Organic Chemistry], Volume E20, pages 80 et seq., Georg Thieme Verlag Stuttgart 1987). Preferably, these are monocarbonyl or dicarbonyl compounds such as benzoin and derivatives thereof, especially benzoin methyl ether, benzil and benzil derivatives, for example 4,4-oxydibenzil, and other dicarbonyl compounds such as diacetyl, 2,3-pentanedione and α-diketo derivatives of norbornane and substituted norbornanes, metal carbonyls such as pentacarbonyl manganese, or quinones such as 9,10-phenanthrenequinone and naphthoquinone. Camphorquinone is particularly preferred.

The formulations according to the invention contain in general 0.01 to 2 parts by weight, preferably 0.1 to 1.5 parts by weight of the initiator, relative to 1 part by weight of the (meth)acrylic acid ester containing formamide groups. If one of the parts to be joined, which is in contact with the adhesive component according to the invention, already contains an initiator of the type described, the initiator in the adhesive component can also be entirely omitted.

The solvents within the scope of the present invention should dissolve the component and, because of the application, should be non-toxic. Water and volatile organic solvents such as methanol, ethanol, propanol, isopropanol, acetone, methyl ethyl ketone, methyl acetate or ethyl acetate may be mentioned as preferred.

In general, 10 to 1,000 parts by weight, preferably 50 to 300 parts by weight, of the solvent, relative to the (meth)acrylic acid ester containing formamide groups, are used.

It can be advantageous to add co-activators, which accelerate the polymerization reaction, to the formulations according to the invention. Examples of known accelerators are amines such as p-toluidine, dimethyl-p-toluidine, trialkylamines such as trihexylamine, polyamines such as N,N,N',N'-tetraalkylalkylenediamine, barbituric acid and dialkylbarbituric acid.

The co-activators are in general employed in a quantity of 0.02 to 4% by weight, preferably 0.2 to 1% by weight, relative to the quantity of polymerizable compounds.

As a further component, the compositions according to the invention can contain carbonyl compounds.

Carbonyl compounds within the scope of the present invention are aldehydes and ketones, which contain 1 to 20, preferably 1 to 10 and particularly preferably 2 to 6 carbon atoms. The carbonyl functional group can be bonded to an aliphatic, aromatic and heterocyclic part of the molecule.

Aliphatic monoaldehydes or dialdehydes may be mentioned as the aldehydes. Formaldehyde, acetaldehyde, propionaldehyde, 2-methylpropionaldehyde, butyraldehyde, benzaldehyde, vanillin, furfural, anisaldehyde, salicylaldehyde, glyoxal, glutaric dialdehyde and phthalic dialdehyde are preferred. Glutaric dialdehyde is particularly preferred.

In particular aliphatic monoketones and diketones may be mentioned as ketones. Butanone, acetone, cyclooctanone, cycloheptanone, cyclohexanone, cyclopentanone, acetophenone, benzophenone, 1-phenyl-2-propanone, 1,3-diphenyl-2-propanone, acetylacetone, 1,2-cyclohexanedione, 1,2-cyclopentanedione and camphorquinone are preferred. Cyclopentanone is particularly preferred.

In general, 1 to 1,000 parts by weight, preferably 5 to 50 parts by weight, of the carbonyl compounds, relative to the (meth)acrylic acid ester containing formamide groups, are employed.

As a further component, the compositions according to the invention can contain (meth)acrylic acid esters which can form crosslinks. (Meth)acrylic acid esters which can form crosslinks can contain in general 2 or more polymerizable active groups in the molecule. Esters of (meth)acrylic acid with dihydric to pentahydric alcohols having 2 to 30 carbon atoms may be mentioned as preferred. Alkoxy(meth)acrylates and (meth)acrylates containing urethane groups are particularly preferred.

(Meth)acrylic acid esters of the formula

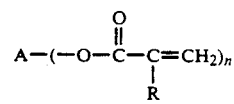

in which

A denotes a straight-chain, branched, cyclic, aliphatic, aromatic or mixed aliphatic-aromatic radical having 2 to 25 C atoms, which can be interrupted by —O—, NH—bridges or O—CO—NH—bridges and can be substituted by hydroxy, oxy, carboxy, amino or halogen, R denotes H or methyl and n represents an integer from 2 to 8, preferably 2 to 4, may be mentioned by way of example.

Preferably, compounds of the following formulae may be mentioned:

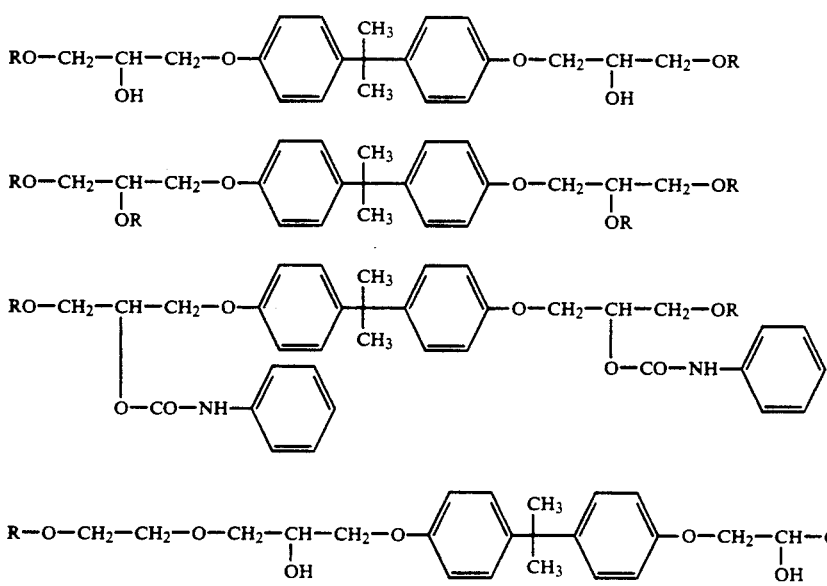

-continued
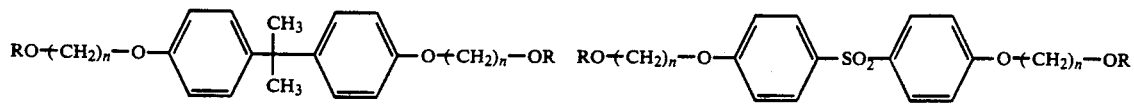
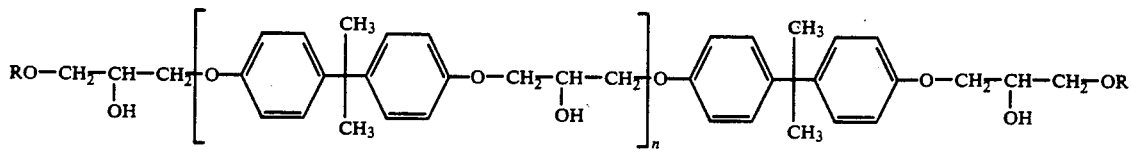
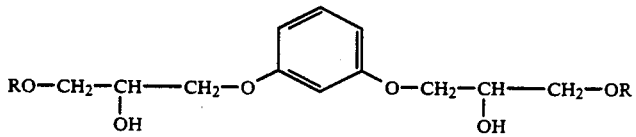
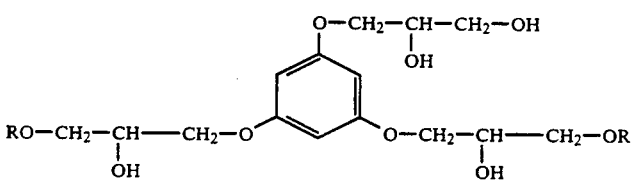
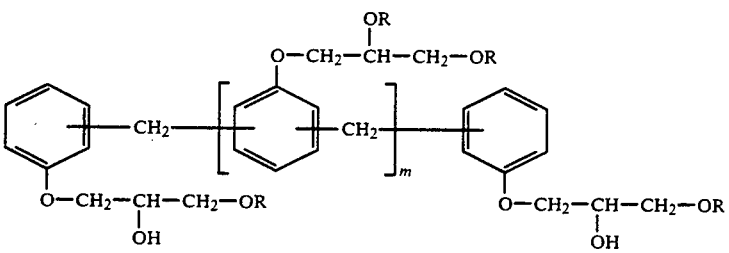
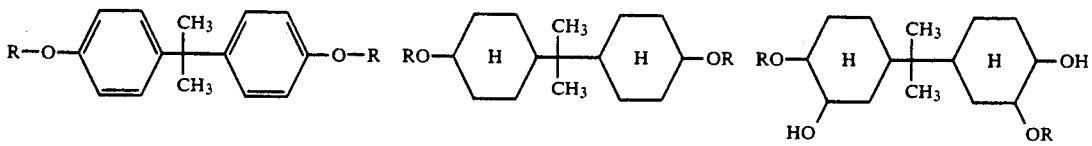
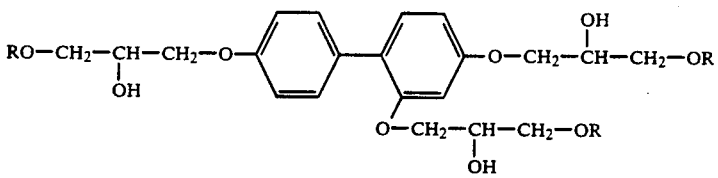
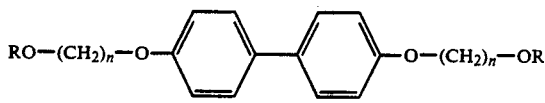
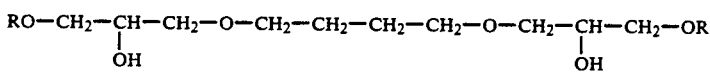
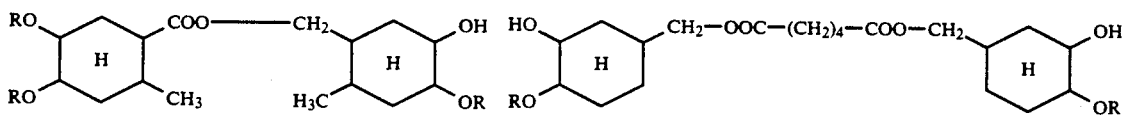

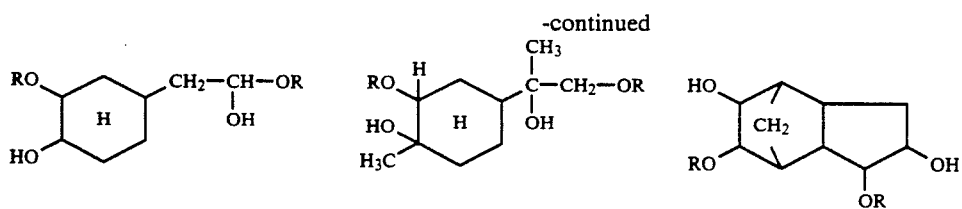
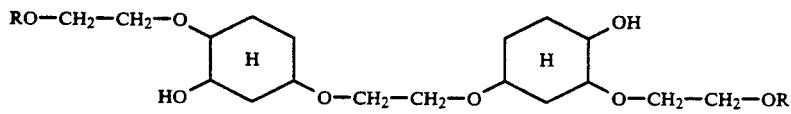
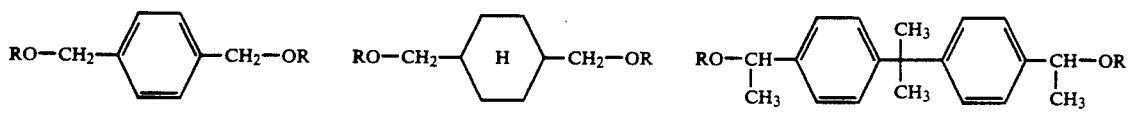
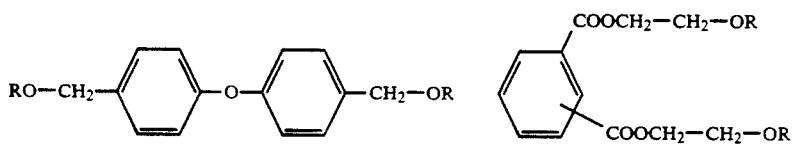
in the ortho, meta or para form
n denotes a number from 1 to 4 and
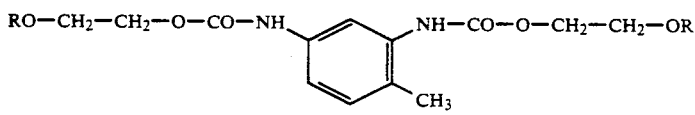
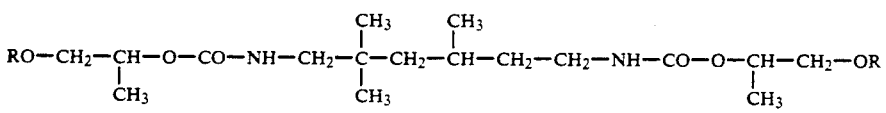
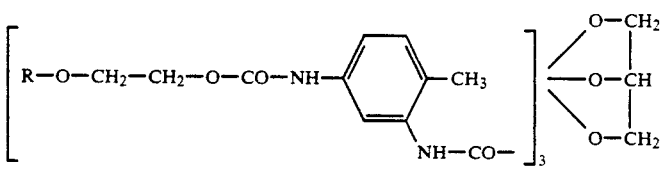
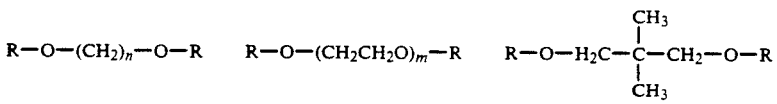
wherein
R represents
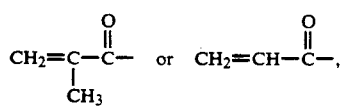
m denotes a number from 0 to 5.
In addition, derivatives of tricyclodecane (EP-A 0,023,686) and reaction products obtained from polyols, diisocyantes and hydroxyalkyl methacrylates (DE-A 3,703,120, DE-3,703,080 and DE-A 3,703,130) may be mentioned. For example, the following monomers may be mentioned:
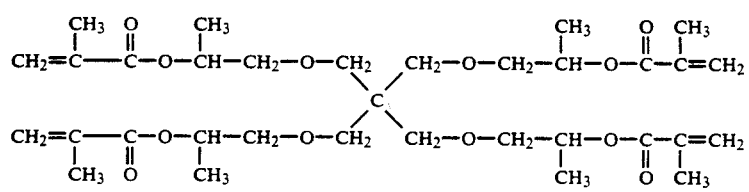

-continued
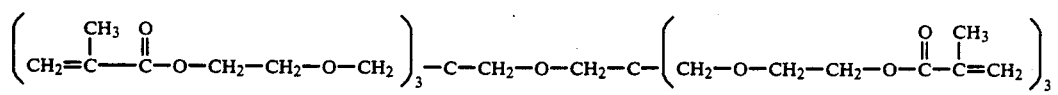
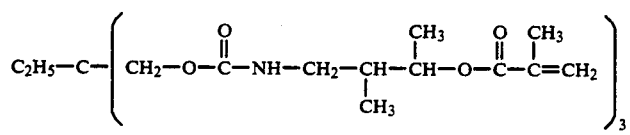
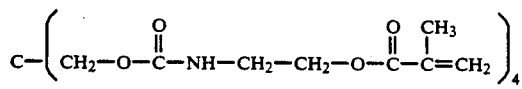
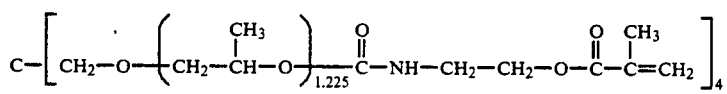
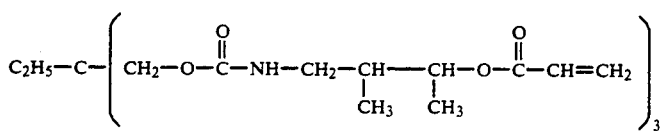
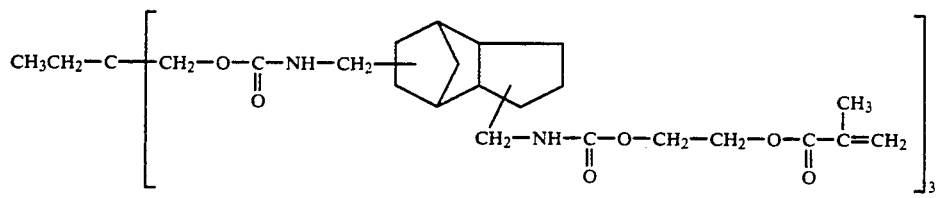
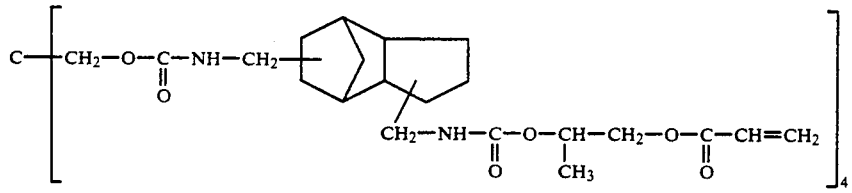
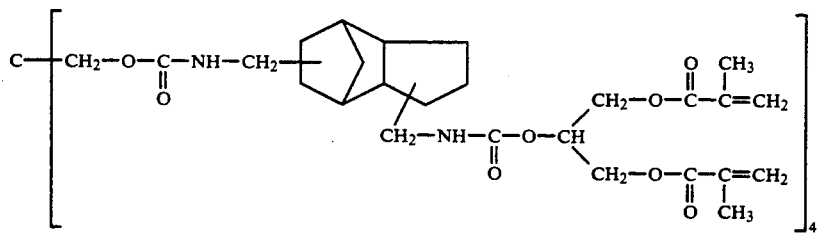
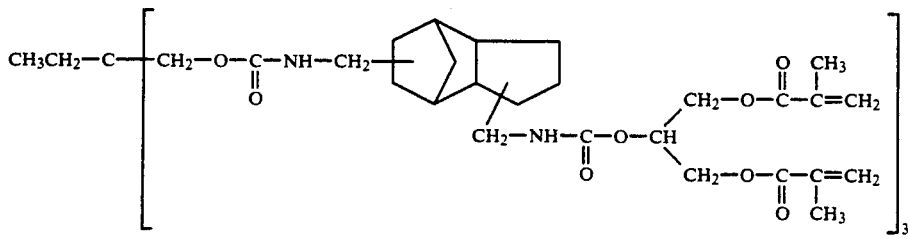

-continued
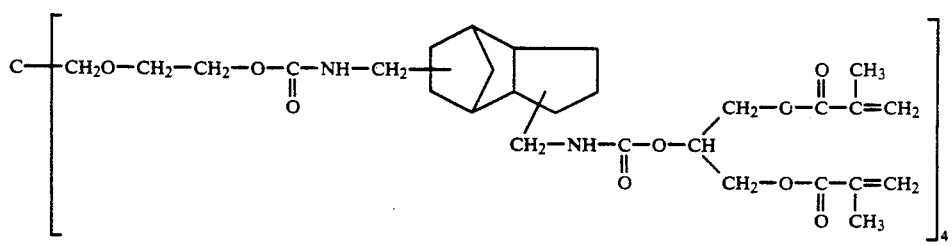
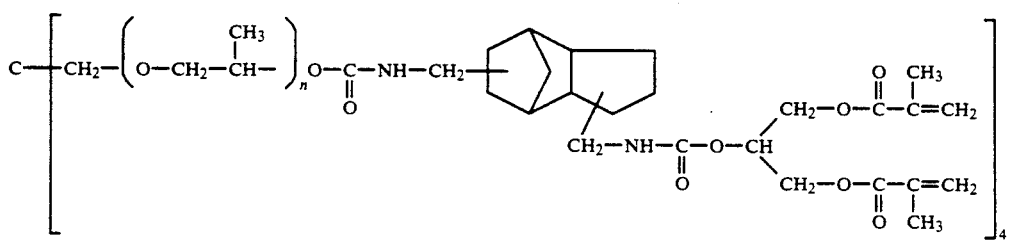
n = 1.225 (statistical mean for 4 chains)
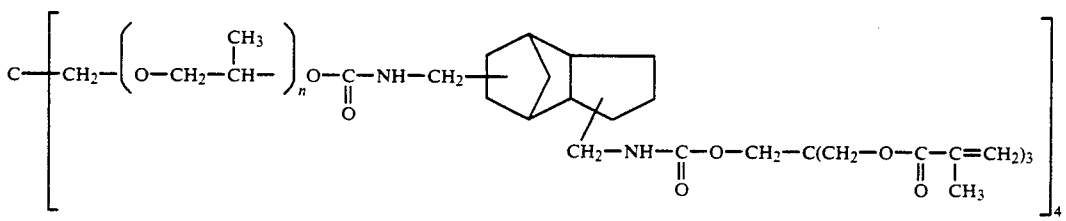
n = 1.225 (mean)
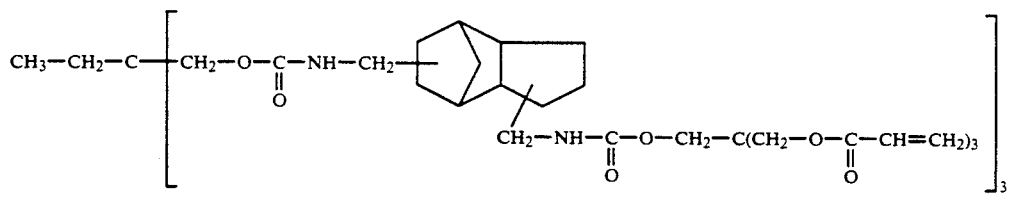
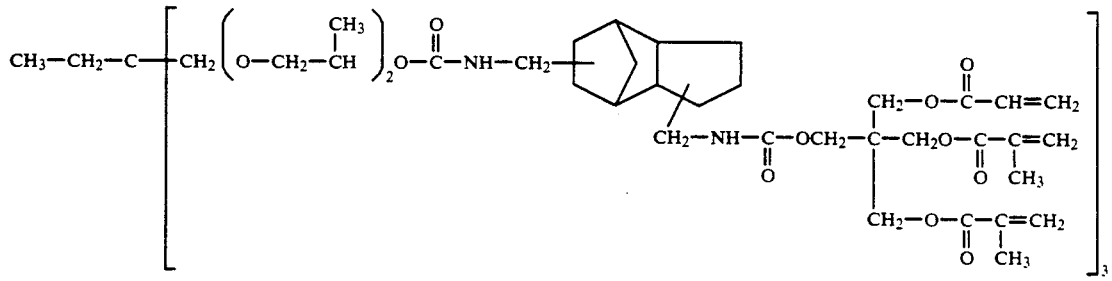

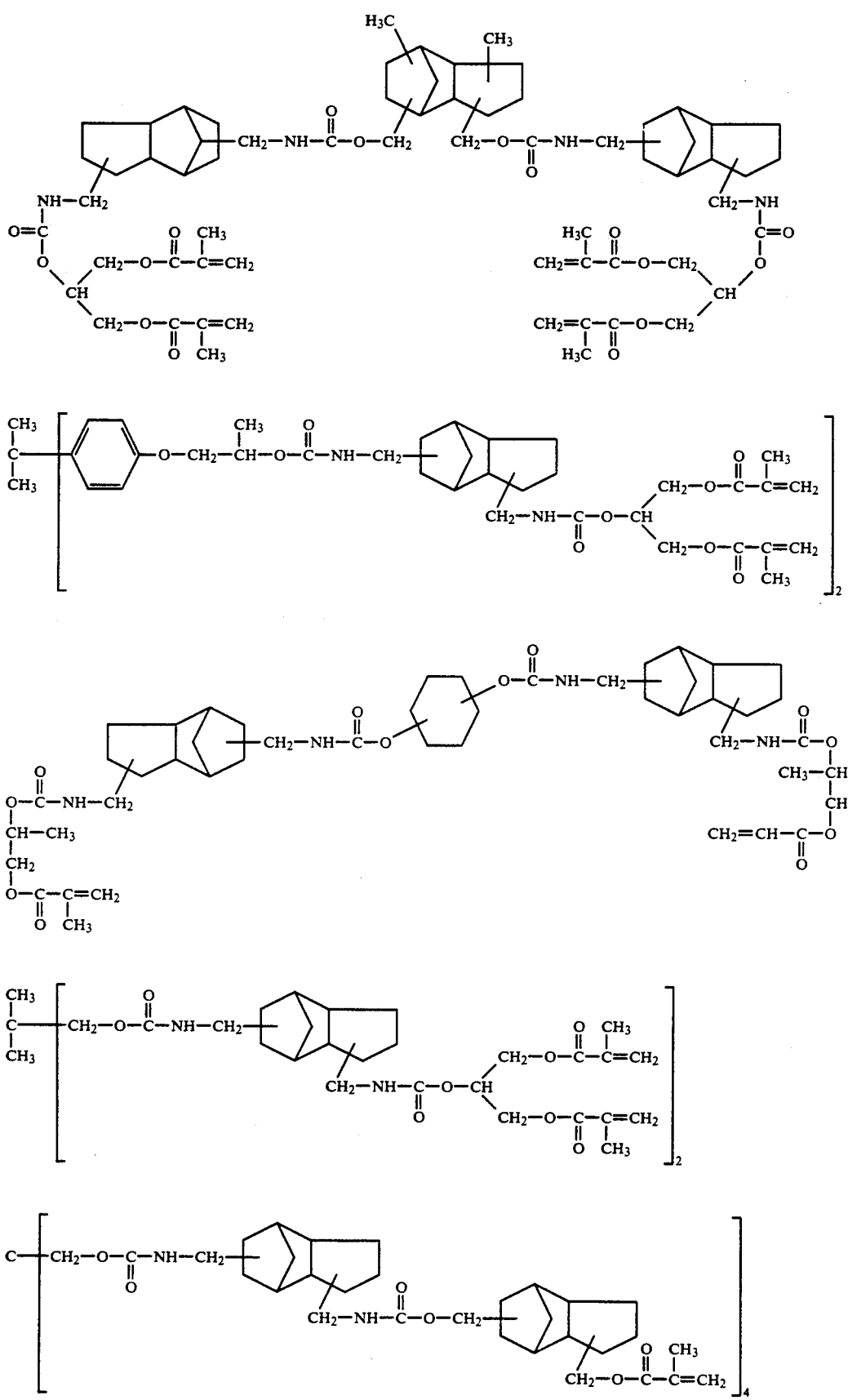

-continued
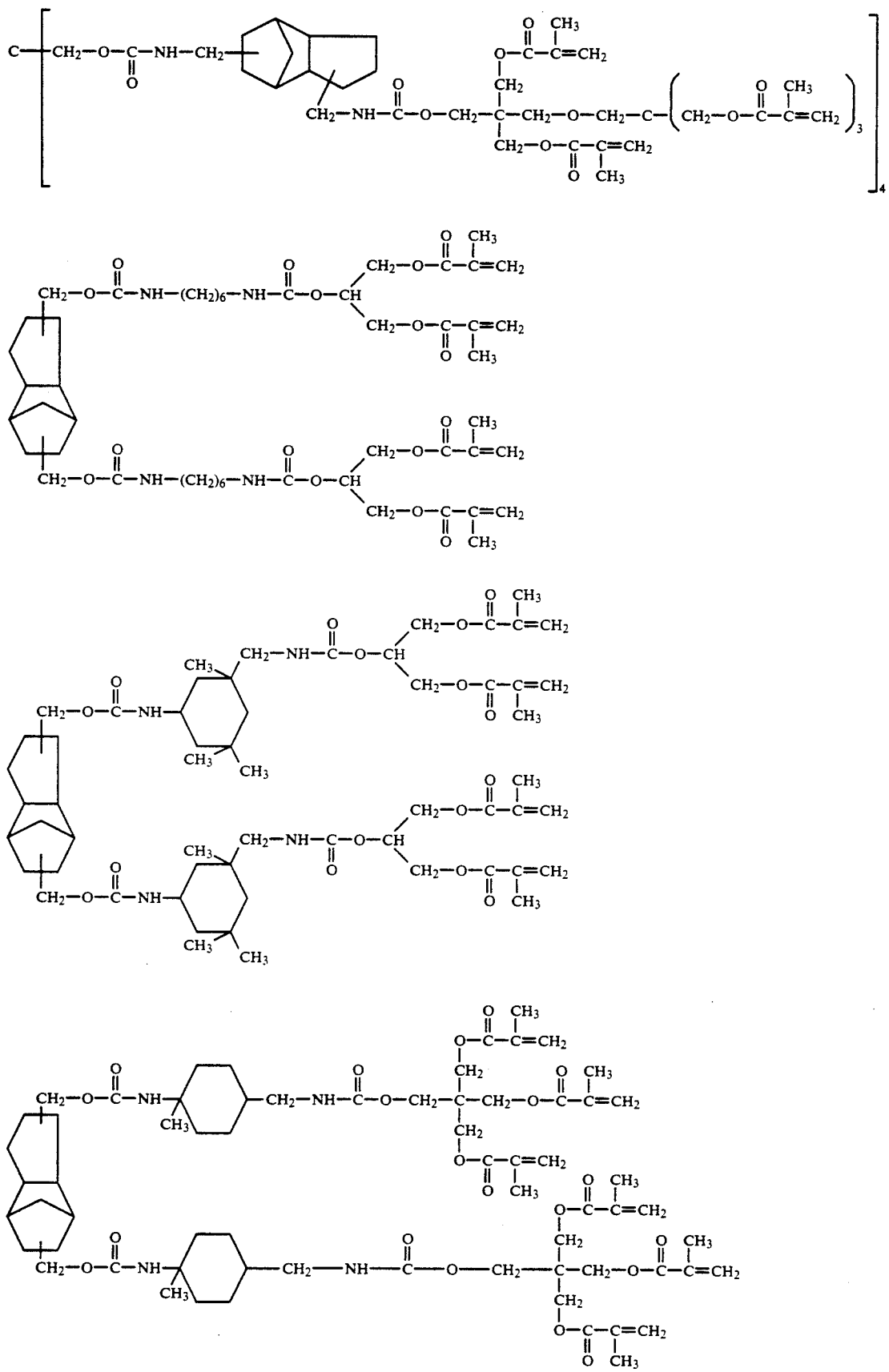

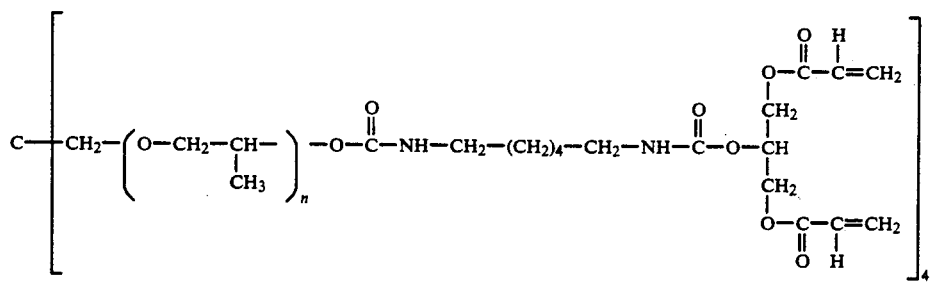

n = 1.225 (statistical mean for 4 chains)

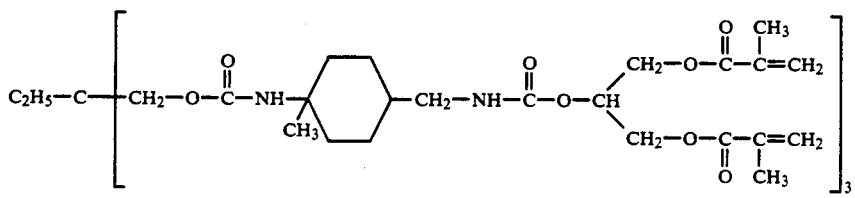

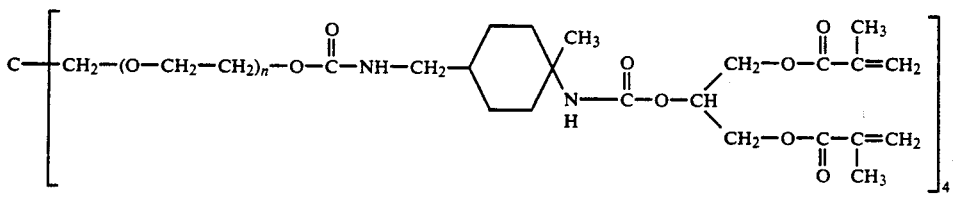

n = 1.225 (statistical mean for 4 chains)

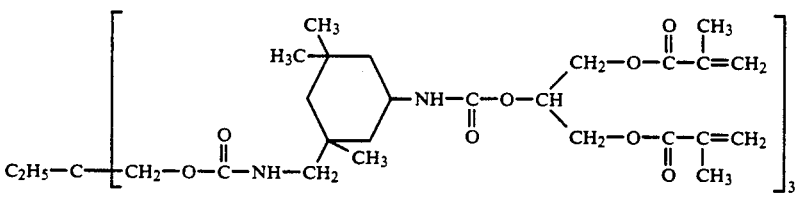

The so-called bis-GMA of the formula

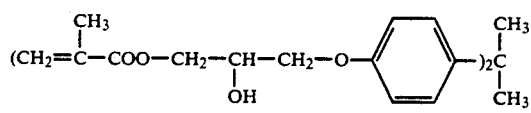

is particularly preferred as the monomer.

Of course, it is possible to use mixtures of the various (meth)acrylic acid esters which can form crosslinks. Mixtures of 20 to 70 parts by weight of bis-GMA and 30 to 80 parts by weight of triethylene glycol dimethacrylate may be mentioned by way of example.

The formulations according to the invention contain in general 5 to 80 parts by weight, preferably 10 to 60 parts by weight, of carboxyl compounds, relative to the (meth)acrylic acid esters containing formamide groups.

As a further component, the compositions according to the invention can contain fillers. The preferred fillers are fine powders which have a particle diameter in the range from 0.1 to 100 μm (optionally also in a polydisperse distribution). Fillers can be fillers usual in the dental field (R. S. Baratz, J. Biomat. Applications, Volume 1, 1987, pages 316 et seq.) such as inorganic glasses, silicon dioxide powder, aluminum oxide power or quartz powder.

As a result of a content of fillers in the formulations according to the invention, adhesive cements are formed which are suitable in particular for fixing bridge materials, crown materials and other veneering materials.

The filler content is in general 20 to 80 parts by weight, preferably 40 to 70 parts by weight, relative to the complete formulation.

The adhesive components according to this invention can also contain up to 10 parts by weight of conventional additives such as stabilizers, inhibitors, light stabilizers, dyestuffs, pigments or fluorescent materials.

The formulations according to the invention can be prepared by mixing the (meth)acrylic acid esters containing formamide groups and the initiator and, if appropriate, the other components by vigorous stirring.

The formulations can also be in a solvent-free form.

The formulations according to the invention can be used as an adhesive component for treating collagen-containing materials.

In a special embodiment, the collagen-containing material is conditioned, before the treatment with the formulation according to the invention, by means of a fluid having a pH value in the range from 0.1 to 3.5.

This contains in general acids having a $pK_s$ value of less than 5 and optionally an amphoteric amino compound having a $pK_s$ value in the range from 9.0 to 10.6 and a $pK_B$ value in the range from 11.5 to 12.5. For example, the following acids can be present in the conditioning fluid: phosphoric acid, nitric acid, pyruvic acid, citric acid, oxalic acid, ethylenediaminetetraacetic acid, acetic acid, tartartic acid, malic acid and maleic acid.

Compounds of the formula $$R^2-\underset{R^3-NH}{\overset{H}{\underset{|}{C}}}-R^1$$

in which
R¹ represents a carboxyl group,
R² denotes hydrogen or a lower alkyl radical which is optionally substituted by hydroxy, thio, methylthio, carboxy, amino, phenyl, hydroxyphenyl or the groups

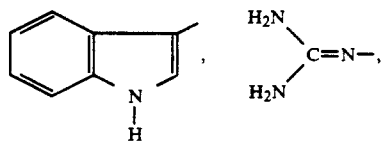

R³ denotes hydrogen or phenyl, it being possible for the radicals R¹ and R³ to be linked by a propyl radical, or in which
R¹ represents hydrogen,
R² represents the group

—A—NH₃X in which
A denotes a bidentate alkylene radical having 1 to 6 carbon atoms and
X represents halogen, and
R³ denotes hydrogen,
may be preferably mentioned as amphoteric amino compounds.

By way of example, the following amphoteric amino compounds may be mentioned: glycine, serine, threonine, cysteine, thyrosine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochoride, butylenediamine hydrobromide, leucine hydrochloride and histidine hydrochloride.

In addition, the conditioning fluid can contain substances from the group comprising the polyethylene glycols and metal hydroxides. In particular, the polybasic acids listed above can also be used as partial metal salts, as long as free acid functional groups remain.

Conditioning fluids which contain at least one of the acids from the group comprising pyruvic acid, ethylenediaminetetraacetic acid and citric acid, as well as optionally an amphoteric amino compound from the group comprising glycine, N-phenylglycine and proline, are particularly preferred.

The application of the formulations according to the invention can be carried out, for example, as follows:

For example in a tooth repair, the conditioning fluid is applied first, for example after mechanical cleaning of the collagen-containing tooth material, by means of a little cotton wool, and is allowed to act for a short time (for example 60 seconds), and the tooth material is rinsed with water and dried in an air stream. The formulation according to the invention is then applied, for example by means of a small brush, in a thin layer which is dried in an air stream. After the treatment according to the invention, the actual filling compound, for example plastic filling compounds usual in the dental field (K. Eichner, "Zahnärztliche Werkstoffe und ihre Verarbeitung" [Dental Materials and their Processing]", Volume 2, pages 135 et seq., Hüthig Verlag, 5th edition 1985), is applied.

The formulations according to the invention can be used in a similar way for fixing crowns, bridges and similar aids.

Example 1 to 9 (Preparation)

The adhesives according to the invention are produced by intensive mixing of the constituents listed in the examples which follow.

Example 1

130 g of water
110 g of methacrylic acid 2-formamidoethyl ester
300 mg of camphorquinone Example 2

130 g of water
110 g of methacrylic acid 3-formamidopropyl ester
300 mg of camphorquinone Example 3

100 g of water
100 g of methacrylic acid 3-formamidopropyl ester
43 g of 25% strength by weight aqueous glutaric dialdehyde solution
300 mg of camphorquinone Example 4

100 g of water
100 g of methacrylic acid 3-formamidopropyl ester
43 g of 25% strength by weight aqueous glutaric dialdehyde solution
76 g of 2-hydroxyethyl methacrylate
300 mg of camphorquinone Example 5

130 g of water
110 g of methacrylic acid 5-formamidopentyl ester
300 mg of camphorquinone Example 6

100 g of water
100 g of methacrylic acid 5-formamidopentyl ester
43 g of 25% strength by weight aqueous glutaric dialdehyde solution
300 mg of camphorquinone Example 7

100 g of water
100 g of methacrylic acid 2-(N-methylformamido)-ethyl ester
43 g of 25% strength by weight aqueous glutaric dialdehyde solution
300 mg of camphorquinone

Example 8

260 g of water
110 g of methacrylic acid 2-(N-methylformamido)-ethyl ester
300 mg of camphorquinone

Example 9

100 g of water
110 g of methacrylic acid 2-(N-hydroxyethylformamido)-ethyl ester
43 g of 25% strength by weight aqueous glutaric dialdehyde solution
300 mg of camphorquinone

Example 10

130 g of water
120 g of methacrylic acid 2-(N-2-hydroxyethylformamido)-ethyl ester
300 mg of camphorquinone
120 mg of isobutyraldehyde
120 mg of 2,6-di-tert.-butyl-4-methylphenol
120 mg of hydroquinone monomethyl ether

Example 11

100 g of water
80 g of acrylic acid 2-formamido ethyl ester
44 g of 25% strength by weight aqueous glutaric dialdehyde solution
300 mg of camphorquinone

Example 12 (Application)

The suitability of the adhesives corresponding to Examples 1 to 11 is tested by determining the bonding strength of the light-activated plastic filling compound based on polyfunctional methacrylic acid esters and barium aluminum silicate Lumifor ® on dentin, which has been pretreated successively with conditioning fluid (consisting of 81.2 g of water, 1.7 g of sodium hydroxide and 17 g of disodium ethylenediaminetetraacetate dihydrate: 60 seconds time of action, rinsing with water, drying with air), with the adhesive (60 seconds time of action, drying with air) and a sealing material based on polyfunctional methacrylic acid esters (Bayer Resin L ®) (applied and thinly distributed in an air stream).

Human teeth, which have been extracted and stored in a moist state, are used for the test. The teeth are embedded in epoxide resin by casting; a smooth dentin surface is produced by re-polishing. Final polishing is carried out with carbon paper 1000.

For preparing a test specimen for measuring the bonding strength, a cylindrical, split Teflon mould is clamped onto the dentin surface which has been treated as described above (Scand. J. Dent. Res. 88, 348-351 (1980)). As the filling compound, a commercially available plastic filling material is filled in. A round drill No. 016, clamped onto a hole in a drill holder, is fixed to the Teflon mould and pressed from above into the layer of material, which is still undergoing the curing process.

The entire arrangement is left to stand undisturbed for 10 minutes at room temperature (25° C.), whereupon the drill holder in the Teflon mould is taken off and the sample is set down under water of a temperature of 23° C. After 15 minutes, the sample with the drill is mounted in an Instron tensile test apparatus (Scand. J. Dent. Res. 88, 348-351 (1980)); a tensile strength measurement is carried out at a speed of 1 mm/minute. The tensile strength is calculated by dividing the load, which is applied when the filling breaks, by the cross-sectional area in the fracture surface of the test specimen. 5 measurements were carried out on each test specimen.

The results are summarized in the table which follows:

| Formulation according to Example No. | Tensile bonding strength [N/mm$^2$] |
|---|---|
| 1 | 22.5 ± 1.1 |
| 2 | 15.0 ± 2.5 |
| 3 | 19.3 ± 2.3 |
| 4 | 19.4 ± 2.1 |
| 5 | 3.7 ± 1.0 |
| 6 | 6.8 ± 2.4 |
| 7 | 19.1 ± 2.0 |
| 8 | 20.0 ± 1.0 |
| 9 | 19.8 ± 2.3 |
| 10 | 15.2 ± 2.2 |
| 11 | 21.7 ± 3.8 |

What is claimed is:

1. In a process of effecting a strong adhesive bonding between a material to be fixed to a collagen-containing material and the collagen-containing material by applying an adhesive component formulation to the collagen-containing material and then fixing the material to be fixed to the collagen-containing material, wherein the improvement comprises the adhesive component formulation consisting of:

(a) one or more (meth)acrylic acid esters, at least one of which contains a formamide group and has the formula

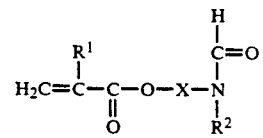

in which
R$^1$ is hydrogen or methyl,
R$^2$ is unsubstituted C$_1$-C$_{12}$-alkyl, C$_6$-C$_{12}$-aryl or C$_7$-C$_{14}$-aralkyl or C$_1$-C$_{12}$-alkyl, C$_6$-C$_{12}$-aryl or C$_7$-C$_{14}$-aralkyl each of which is substituted by hydroxy, carboxy, halogen or amino of the formula

R$^3$ and R$^4$ each independently are lower alkyl and
X denotes an unsubstituted divalent C$_1$-C$_{24}$-aliphatic or C$_5$-C$_8$-cycloaliphatic or C$_6$-C$_{12}$-aromatic radical each of which can optionally contain one or more oxygen bridges, sulphur bridges or —NR$^3$ bridges, or a divalent C$_1$-C$_{24}$-aliphatic or C$_5$-C$_8$-cycloaliphatic or C$_6$-C$_{12}$-aromatic radical each of which is substituted by hydroxy-, carboxy-, halogen- or amino of the formula

and each of which can optionally contain one or more oxygen bridges, sulphur bridges of —NR$_3$ bridges;
(b) optionally at least one initiator selected from the group consisting of benzoin methyl ether, benzil derivatives, diacetyl, 2,3-pentanedione, α-diketo derivatives of norbornane and substituted norbornanes, metal carbonyls, and quinones;
(c) optionally at least one solvent;
(d) optionally at least one coactivator;
(e) optionally at least one filler; and
(f) optionally at least one (meth)acrylic acid ester, which can form crosslinks, said (meth)acrylic acid esters being of the formula

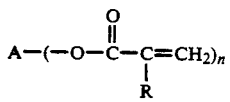

in which

A denotes a straight-chain, branched, or cyclic aliphatic, aromatic or mixed aliphatic-aromatic radical having 2 to 25 C atoms, each of which can be interrupted by —O—, NH—bridges or —CO—N-H—bridges and can be substituted by hydroxy, oxy, carboxy, amino or halogen, R denotes H or methyl and n represents an integer from 2 to 8.

2. A method according to claim 1, wherein, prior to applying the adhesive component formulation, conditioning the collagen-containing with a fluid of a pH value from 0.1 to 3.5.

3. A method according to claim 1, wherein the collagen-containing material is a tooth.

4. A method according to claim 1 wherein the collagen-containing material is bone.

5. A method according to claim 1, wherein
R$^1$ is hydrogen or methyl,
R$^2$ is unsubstituted, C$_1$-C$_6$-alkyl, phenyl, tolyl, benzyl or methyl-substituted benzyl, or C$_1$-C$_6$-alkyl, phenyl, tolyl or benzyl substituted by hydroxy, carboxy, fluorine or amino and
X denotes an unsubstituted divalent C$_1$-C$_{20}$-aliphatic or C$_5$-C$_6$-cycloaliphatic or C$_6$-C$_{12}$-aromatic radical each of which optionally can contain one to ten oxygen bridges or —NR$^3$—bridges, or a divalent C$_1$-C$_{20}$-aliphatic or C$_5$-C$_6$-cycloaliphatic or C$_6$-C$_{12}$-aromatic radical each of which is substituted by hydroxy, carboxy, fluorine, chlorine or amino and each of which optionally can contain one to ten oxygen bridges or —NR$^3$—bridges.

6. A method according to claim 1, wherein
R$^1$ is hydrogen or methyl,
R$^2$ is unsubstituted C$_1$-C$_6$-alkyl, phenyl or tolyl or C$_1$-C$_6$-alkyl. phenyl or tolyl each of which is substituted by hydroxy-, carboxy-, fluorine, chlorine- or amino and
X denotes an unsubstituted divalent C$_1$-C$_8$-aliphatic or C$_5$-C$_6$-cycloaliphatic or phenylene radical each of which can optionally contain one to four oxygen bridges, or a divalent C$_1$-C$_8$-aliphatic or C$_5$-C$_6$-cycloaliphatic or phenylene radical each of which is substituted by hydroxy, carboxy, fluorine, chlorine or amino and each of which can optionally contain one to four oxygen bridges.

7. A method according to claim 1, wherein the (meth)acrylic acid ester containing formamide groups and the initiator are dissolved in a solvent.

8. A method according to claim 1, wherein the adhesive component formulation contains a coactivator.

9. A method according to claim 1, wherein the adhesive component formulation contains a (meth)acrylic acid ester, which can form crosslinks, said (meth)acrylic acid esters being of the formula

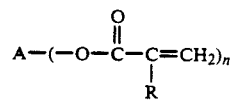

in which

A denotes a straight-chain, branched or cyclic aliphatic, aromatic or mixed aliphatic-aromatic radical having 2 to 25 C atoms, each of which can be interrupted by —O—, NH—bridges or O—CO—NH—bridges and can be substituted by hydroxy, oxy, carboxy, amino or halogen, R denotes H or methyl and n represents an integer from 2 to 8.

10. A method according to claim 1, wherein the adhesive component formulation contains a filler.

11. A method according to claim 9, wherein n represents an integer from 2 to 4.

* * * * *

UNITED STATES PATENT AND TRADEMARK OFFICE
CERTIFICATE OF CORRECTION

PATENT NO. : 5,277,739
DATED : January 11, 1994
INVENTOR(S) : Muller, et al.

It is certified that error appears in the above-indentified patent and that said Letters Patent is hereby corrected as shown below:

Col. 25, line 24   After " bridges or " insert -- 0 --

Col. 25, line 31   After " containing " insert -- material --

Signed and Sealed this

Eighth Day of July, 1997

Attest:

Attesting Officer

BRUCE LEHMAN

Commissioner of Patents and Trademarks